(12) United States Patent
Mumford et al.

(10) Patent No.: US 7,575,005 B2
(45) Date of Patent: Aug. 18, 2009

(54) MASK ASSEMBLY WITH INTEGRATED SENSORS

(75) Inventors: John Robert Mumford, Mississauga (CA); Ronald Leon Kurtz, Oakville (CA); Jianping Wu, Misissauga (CA)

(73) Assignee: Excel-Tech Ltd., Oakville, Ontario (CA)

( * ) Notice: Subject to any disclaimer, the term of this patent is extended or adjusted under 35 U.S.C. 154(b) by 764 days.

(21) Appl. No.: 11/131,284

(22) Filed: May 18, 2005

(65) Prior Publication Data

US 2005/0268916 A1 Dec. 8, 2005

Related U.S. Application Data

(60) Provisional application No. 60/571,890, filed on May 18, 2004, provisional application No. 60/571,944, filed on May 18, 2004, provisional application No. 60/571,942, filed on May 18, 2004.

(51) Int. Cl.
*A62B 9/00* (2006.01)
(52) U.S. Cl. .............................. 128/205.23; 128/206.21; 600/544
(58) Field of Classification Search ............ 128/205.23, 128/206.21, 205.25, 206.11, 206.12, 206.18, 128/206.24, 206.26, 206.27, 206.28, 207.11, 128/207.13, 27.18; 600/534, 537, 538, 544, 600/545
See application file for complete search history.

(56) References Cited

U.S. PATENT DOCUMENTS

| | | | |
|---|---|---|---|
| 3,313,293 A | 4/1967 | Chesebrough et al. | |
| 3,669,119 A | 6/1972 | Symmes | |
| 3,675,649 A | 7/1972 | Basham et al. | |
| 4,928,696 A | 5/1990 | Henderson et al. | |
| 5,245,995 A | 9/1993 | Sullivan et al. | |
| 5,280,791 A | 1/1994 | Lavie | |
| 5,353,788 A | 10/1994 | Miles | |
| 5,398,682 A | 3/1995 | Lynn | |
| 5,479,934 A | 1/1996 | Imran | |
| 5,485,851 A | 1/1996 | Erickson | |
| 5,645,054 A | 7/1997 | Cotner et al. | |
| 5,662,101 A | 9/1997 | Ogden et al. | |
| 5,682,878 A | 11/1997 | Ogden | |
| 5,794,615 A | 8/1998 | Estes | |
| 5,803,065 A | 9/1998 | Zdrojkowski et al. | |

(Continued)

OTHER PUBLICATIONS

Multi-Centre Comparison of Five Eye Movement Detection Algorithms. Journal of Sleep Research, 4, pp. 119-130, 1995.

(Continued)

*Primary Examiner*—Steven O Douglas
(74) *Attorney, Agent, or Firm*—Bereskin & Parr LLP/S.E.N.C.R.L., s.r.l.

(57) ABSTRACT

Embodiments of the invention relate to a mask assembly for use in treatment systems for treating obstructive sleep apnea using continuous positive air pressure (CPAP). The mask assembly comprises a mask or nasal interface for supplying gas to the nose of a wearer of the mask assembly. The mask assembly also comprises a strap or harness attached to the mask for securing the mask assembly to the wearer and sensors located on the mask assembly for measuring physiological signals of the wearer. These physiological signals are communicated to a monitoring unit which, in association with a CPAP device, serves to determine the efficacy of the CPAP treatment and to vary operational parameters of the treatment.

29 Claims, 9 Drawing Sheets

U.S. PATENT DOCUMENTS

| | | | |
|---|---|---|---|
| 5,901,704 | A | 5/1999 | Estes et al. |
| 5,904,141 | A | 5/1999 | Estes et al. |
| 5,970,975 | A | 10/1999 | Estes et al. |
| 5,999,846 | A | 12/1999 | Pardey et al. |
| 6,032,065 | A | 2/2000 | Brown |
| 6,085,747 | A | 7/2000 | Axe et al. |
| 6,091,973 | A | 7/2000 | Colla et al. |
| 6,128,521 | A | 10/2000 | Marro et al. |
| 6,138,675 | A | 10/2000 | Berthon-Jones |
| 6,230,049 | B1 | 5/2001 | Fichell et al. |
| 6,240,921 | B1 | 6/2001 | Brydon et al. |
| 6,272,378 | B1 | 8/2001 | Baumgart-Schmitt |
| 6,363,270 | B1 | 3/2002 | Colla et al. |
| 6,397,845 | B1 | 6/2002 | Burton |
| 6,427,689 | B1 | 8/2002 | Estes et al. |
| 6,431,171 | B1 | 8/2002 | Burton |
| 6,467,477 | B1 | 10/2002 | Frank et al. |
| 6,539,940 | B2 | 4/2003 | Zdrojkowski et al. |
| 6,564,797 | B1 | 5/2003 | Mechlenburg et al. |
| 6,609,517 | B1 | 8/2003 | Estes et al. |
| 6,629,527 | B1 | 10/2003 | Estes et al. |
| 6,640,806 | B2 | 11/2003 | Yurko |
| 6,654,626 | B2 | 11/2003 | Devlin et al. |
| 6,826,426 | B2 | 11/2004 | Lange et al. |
| D505,489 | S * | 5/2005 | Sleeper .................. D24/110.1 |
| 6,993,380 | B1 | 1/2006 | Modarres |
| 7,204,250 | B1 * | 4/2007 | Burton .................. 128/205.23 |
| 7,282,027 | B2 * | 10/2007 | Sotos et al. ................. 600/300 |
| 2002/0029004 | A1 | 3/2002 | Starr et al. |
| 2003/0172936 | A1* | 9/2003 | Wilkie et al. ........... 128/207.18 |
| 2004/0045551 | A1* | 3/2004 | Eaton et al. ............ 128/206.21 |
| 2004/0204656 | A1 | 10/2004 | Tolvanen-Laakso et al. |
| 2005/0059898 | A1 | 3/2005 | Gobel |
| 2005/0261559 | A1 | 11/2005 | Mumford et al. |
| 2005/0268916 | A1 | 12/2005 | Mumford et al. |
| 2006/0258930 | A1 | 11/2006 | Wu et al. |

OTHER PUBLICATIONS

+/− 1.5g-3g Three Axis Low-g Micromachined Accelerometer. www.freescale.com, accessed May 2006.

Customised Printed Circuit Sensors & Electrodes. www.vermed.com/custom.php, accessed May 2006.

Chen et al., "A Comparison of Patient State Index and Bispectral Index Values During the Perioperative Period", Society for Technology in Anesthesia, 2002, pp. 1669-1674.

Gora et al., "Evidence of a Sleep-Specific Blunted Cortical Response . . . ", American Journal of Respiratory and Critical Care Medicine, vol. 166, 2002, pp. 1225-1234.

* cited by examiner

MASK ASSEMBLY WITH INTEGRATED SENSORS

RELATED APPLICATIONS

This application claims the benefit of U.S. Provisional Patent Application Ser. No. 60/571,942, filed May 18, 2004, the entire contents of which is hereby incorporated by reference, U.S. Provisional Patent Application Ser. No. 60/571,890, filed on May 18, 2004, the entire contents of which is hereby incorporated by reference and U.S. Provisional Patent Application Ser. No. 60/571,942 filed on May 18, 2004, the entire contents of which are hereby incorporated by reference.

FIELD OF THE INVENTION

This invention relates to a mask assembly that is used for the detection of physiological information and the treatment of medical conditions. More particularly, this invention relates to a mask assembly with integrated sensors for sensing the efficacy of treatment of medical conditions.

BACKGROUND OF THE INVENTION

Obstructive Sleep Apnea (OSA) is a life-threatening condition characterized by frequent episodes in which an individual stops breathing or breathes less efficiently during sleep. OSA is caused by a blockage of the airway typically resulting from the collapse and closure of the soft tissue in the rear of the throat during sleep. With each apnea event, the brain arouses the individual in order for the individual to resume breathing, but consequently sleep is extremely fragmented and of poor quality.

According to the National Institute of Health, OSA currently affects more than twelve million Americans (4% of men and 2% of women), making this disorder as common as adult diabetes. Further, the disrupted and/or poor quality sleep that is associated with OSA may lead to serious health issues including hypertension, heart disease, diabetes, and stroke. Moreover, untreated sleep apnea may be responsible for job impairment and motor vehicle crashes. For example, the Department of Transport in the UK estimates that 20% of road accidents leading to death and serious injury are caused by drowsiness or sleep disorders.

When an individual is diagnosed with OSA, the individual may be prescribed a therapeutic regime involving the use of a Continuous Positive Airway Pressure (CPAP) device. The CPAP device works by delivering a steady flow of air through a soft, pliable mask worn over the individual's nose. The CPAP device essentially pressurizes the throat of the individual thereby preventing the collapse of the soft tissue and keeping the airways open and allowing the individual to breathe uninterrupted during sleep.

The CPAP device is both loud and uncomfortable and has met with various non-compliance issues. However, it is possible to augment the CPAP device to control gas delivery to the individual according to changes in the physiological state of the wearer. These changes can be seen in brainwave patterns, blood oxygen saturation and breathing patterns. One or more of the individual's EEG, EOG, EMG, position, breathing and blood oxygen levels can be monitored by a monitor unit associated with the CPAP device. In some instances, the monitoring unit may be part of the CPAP device. The EEG is used to observe brain activities during sleep. The EMG is used to observe muscle tone during sleep. The EOG is used to observe eye movement during sleep. The three physiological signals (i.e. EEG, EOG, and EMG) may be used together to score sleep stages.

Arousals due to upper airway resistance may be detected from a shift in frequency of the patient's EEG and/or EOG as well as a decrease in blood oxygen levels. The monitoring unit includes an algorithm that detects the arousals and sleep stages, and uses the physiological information to automatically adjust the delivered respiratory gas pressure to the CPAP device wearer based on the physiological information. The algorithm can also use the physiological information to determine the effectiveness of the treatment.

In order to measure the physiological information, various sensors are attached to the CPAP patient. For instance, to measure EEG, EOG and EMG, several electrodes may be applied to the patient's head and face. To measure blood oxygen level, a blood oximetry probe may be applied to the patient's finger or earlobe. To measure body position, an accelerometer-based sensor may be placed on the patient's chest. These sensors are connected to the monitoring unit with appropriate electrical wires. Once the sensors are applied, the CPAP device wearer puts on the mask assembly. The mask assembly includes a nasal mask (or a nasal/oral mask) and a harness that maintains the position of the nasal mask on the face of the wearer.

However, the application of electrodes by the CPAP device wearer is not an easy process; it is difficult, time consuming and prone to errors. The process involves preparing the site to reduce impedance, attaching one electrode at a time with tape and/or adhesives, and then individually wiring each electrode to the monitoring unit. In a clinical setting, the electrodes are typically positioned by a polysomnography technician according to standard positions, or as directed by a physician. In a non-clinical setting, such as at a patient's home, the patient or another untrained person may be required to position the electrodes on the patient. Such untrained persons may have difficulty placing the electrodes in the correct location or correctly wiring the electrode to the monitoring unit. Even in a clinical setting, a trained technician may position an electrode incorrectly.

Furthermore, once the electrodes and the other sensors are applied to the wearer and connected to the monitoring unit, the arrangement results in many wires emanating from different locations on the wearer to the monitoring unit. As a result, the arrangement is uncomfortable for the wearer and interferes with the wearer's natural movements, which makes it difficult for the wearer to sleep. Consequently, the wearer may find it difficult to find a comfortable sleep position. In addition, the wearer may move during sleep such that the sensors become disconnected from the monitoring unit. Also, motion of the wires connecting the electrodes to the monitoring unit introduces electrical artifacts that hides the underlying physiological information. These technical difficulties also prevent sleep studies from being conducted at a patient's home. Further, the unfamiliar environment in the sleep lab may dramatically affect the patient's sleep which in turn may lead to an inaccurate diagnosis.

It is desired to address or ameliorate one or more of the shortcomings, disadvantages or problems associated with prior systems or devices, or to at least provide a useful alternative thereto.

SUMMARY OF THE INVENTION

The invention relates to a mask assembly with integrated sensors for sensing the efficacy of treatment of medical conditions, such as obstructive sleep apnea during treatment with continuous positive airway pressure.

In one aspect, the invention provides a mask assembly adapted to be worn by a wearer for treatment of a medical condition. The mask assembly comprises a mask shaped to fit over at least the nose of the person, the mask including a gas inlet for providing pressurized gas to the wearer; a harness assembly attached to the mask, the harness assembly including a plurality of straps for securing the mask assembly to the head of the wearer; and, sensors located on the mask assembly for providing physiological information about the person for determining efficacy of treatment and for varying operational parameters of the treatment, the sensors being located on at least one of the mask and the harness assembly.

In one embodiment, the sensors include electrodes. Preferably, the sensors include three electrodes arranged in a triangular configuration with at least a portion of the configuration being disposed on a forehead of the wearer.

In another embodiment, the mask includes a vertical mounting plate extending upwardly from the top of the mask and wherein a first electrode is located at the mask at the nasion of the person and a second electrode is located at the vertical mounting plate at the central forehead region of the person.

In another embodiment, the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, wherein a first electrode is located at the mask at the nasion of the person, a second electrode is located at the upper right strap horizontally offset with respect to the center of the right eye of the wearer, and a third electrode is located at the upper left strap horizontally offset with respect to the center of the left eye of the wearer.

In another embodiment, the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, right and left lower straps that engage elongated apertures at the bottom of the mask, a right vertical strap behind the right ear of the wearer that connects the right upper strap to the right lower strap and a left vertical strap behind the left ear of the wearer that connects the left upper strap to the left lower strap, the right and left vertical straps located proximally to the right and left mastoids of the wearer, wherein a first electrode is located at the upper right strap horizontally offset with respect to the center of the right eye of the wearer, a second electrode is located at the upper left strap horizontally offset with respect to the center of the left eye of the wearer, and a third electrode is located at one of the right and left vertical straps proximally to the corresponding mastoid of the wearer.

In another embodiment, the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, right and left lower straps that engage elongated apertures at either side near the bottom of the mask, a right vertical strap behind the right ear of the wearer that connects the right upper strap to the right lower strap and a left vertical strap behind the left ear of the wearer that connects the let upper strap to the left lower strap, the right and left vertical straps located proximally to the right and left mastoids of the wearer, wherein a first electrode is located at the vertical mounting plate at the central forehead region of the wearer and a second electrode is located at one of the right and left vertical straps proximally to the corresponding mastoid of the wearer.

In a further embodiment, the mask includes a forehead support member extending vertically from the top of the mask, the forehead support member having right and left horizontal ends that extends above the eyebrows of the wearer, wherein a first electrode is located at the mask at the nasion of the wearer, a second electrode is located at the right horizontal end of the forehead support member above the right eyebrow of the wearer and horizontally offset with respect to the center of the right eye of the wearer, and a third electrode is located at the left horizontal end of the forehead support member above the left eyebrow of the wearer and horizontally offset with respect to the center of the left eye of the wearer.

In another embodiment, the sensors further include a blood oximeter sensor. The blood oximeter sensor may be located at the forehead support member in close proximity to the forehead of the wearer. The sensors may further include a pressure transducer sensor disposed within the mask.

In another embodiment, the sensors further include a position sensor. Preferably, the mask includes a forehead support member extending vertically therefrom, the position sensor being located at the forehead support member. Preferably, the sensors further include at least two of a blood oximeter sensor, a pressure transducer and a position sensor.

In another embodiment, the mask assembly further includes a remote processing unit connected to the sensors for processing the physiological information. The remote processing unit may include a sleep efficacy algorithm for processing the physiological information and generating a sleep information profile for the wearer. Preferably, the remote processing unit includes a wireless transceiver for wirelessly transmitting signals related to the physiological information, and a battery for providing power to the remote processing unit.

In another aspect, the invention relates to a mask assembly adapted to be worn by a wearer for treatment of a medical condition. The mask assembly comprises a mask shaped to fit over at least the nose of the person, the mask including a gas inlet for providing pressurized gas to the wearer; a harness assembly attached to the mask, the harness assembly including a plurality of straps for securing the mask assembly to the head of the wearer; and, at least two electrodes located on the inside of the mask assembly and being spaced with regards to one another for sensing physiological information including at least one of the EEG, EMG and EOG of the wearer whereby the physiological information is used to monitor the efficacy of treatment or to vary operational parameters of the treatment, the at least two electrodes being located on at least one of the mask and the harness assembly.

In yet another aspect, the invention relates to a mask assembly adapted to be worn by a wearer for treatment of a medical condition, the mask assembly including sensors located on the mask assembly for sensing physiological information from the wearer and a remote processing unit located on the mask assembly and connected to the sensors for processing the physiological information.

In a further aspect, the invention relates to a mask assembly for wearing by a wearer for treatment of a medical condition. The mask assembly comprises a nasal interface for providing pressurized gas to the wearer, the nasal interface comprising a gas inlet for receiving a source of gas and a gas outlet for providing gas directly to the nares of the wearer. The mask assembly further comprises at least one strap or other harness means connected to the nasal interface for securing the mask assembly to the head of the wearer. The mask assembly also has sensors located on the mask assembly for measuring physiological signals of the wearer during treatment of the medical condition to determine efficacy of the treatment and to vary operational parameters of the treatment. The sensors are located on at least one of the strap or forehead member of the mask assembly.

The forehead member preferably comprises at least two electrodes disposed so as to contact the skin of the forehead of the wearer of the mask assembly during treatment so that the electrodes can pick up the physiological signals. Such physiological signals may be electromyography (EMG), electroencephalography (EEG) or eletroocularography (EOG) signals.

Preferably, the nasal interface comprises a gas supply tube in fluid communication with the gas source and passing between the mouth and the nose of the wearer. The nasal interface comprises two neris feed portions for feeding gas into the nostrils of the wearer and substantially occluding the nostrils against airflow other than through the nasal interface.

In a still further aspect, the invention relates to an electrode placement assembly for locating electrodes on the forehead of a wearer of the electrode placement assembly. The electrode placement assembly comprises a forehead placement assembly, at least one strap and at least two electrodes. The forehead placement assembly is dimensioned to extend laterally across a forehead of the wearer and has a lower portion for at least partly overlying a nasion area of the wearer. The at least one strap is connected to the forehead placement assembly for securing the electrode placement assembly to the wearer. The at least two electrodes are positioned on at least one of the forehead placement assembly and the at least one strap so that the at least two electrodes contact the skin of the wearer.

The electrode placement assembly preferably comprises attachment means for attaching a nasal interface to the electrode placement assembly so that the nasal interface is positioned to provide gas to the neres of the wearer. The attachment means may comprise flexible attachment members for attaching the nasal interface to the at least one strap. Alternatively, the attachment means may comprise a connector member positioned on the forehead placement assembly for connecting the nasal interface to the forehead placement assembly.

In one embodiment, the forehead placement assembly may be formed of a unitary flexible plate. Alternatively, the forehead placement assembly may be comprised of separate interconnected members. Preferably, one of the at least two electrodes is positioned on the lower portion of the forehead placement assembly for at least partly overlying the nasion area. Another of the at least two electrodes may be positioned on the forehead placement assembly away from the one electrode for overlying an area of the forehead vertically displaced from the nasion area. This other electrode may be positioned centrally above the forehead or on either lateral side above, or extending laterally of, the pupils of the wearer.

In one particular embodiment, the electrode placement assembly comprises four electrodes. Three of these electrodes are located on the forehead placement assembly for positioning laterally across the forehead of the wearer. A fourth electrode is located on the lower portion of the forehead placement for at least partly overlying the nasion area.

Advantageously, the electrode placement assembly can be used with different nasal interfaces, according to the particular nasal interface design preferred by the wearer. For example, some wearers may prefer a mask which covers the entire nose while other wearers may prefer less obtrusive tubing to lie across the upper lip and beneath the nose and having gas outlets feeding directly into the neres of the wearer.

BRIEF DESCRIPTION OF THE DRAWINGS

For a better understanding of the invention and to show more clearly how it may be carried into effect, reference will now be made, by way of example only, to the accompanying drawings which show exemplary embodiments of the invention and in which:

FIG. 2b is a side view of the mask assembly of FIG. 2a;

FIG. 5b is a block diagram of the remote processing unit of FIG. 5a;

DETAILED DESCRIPTION OF EMBODIMENTS OF THE INVENTION

Figure 1:
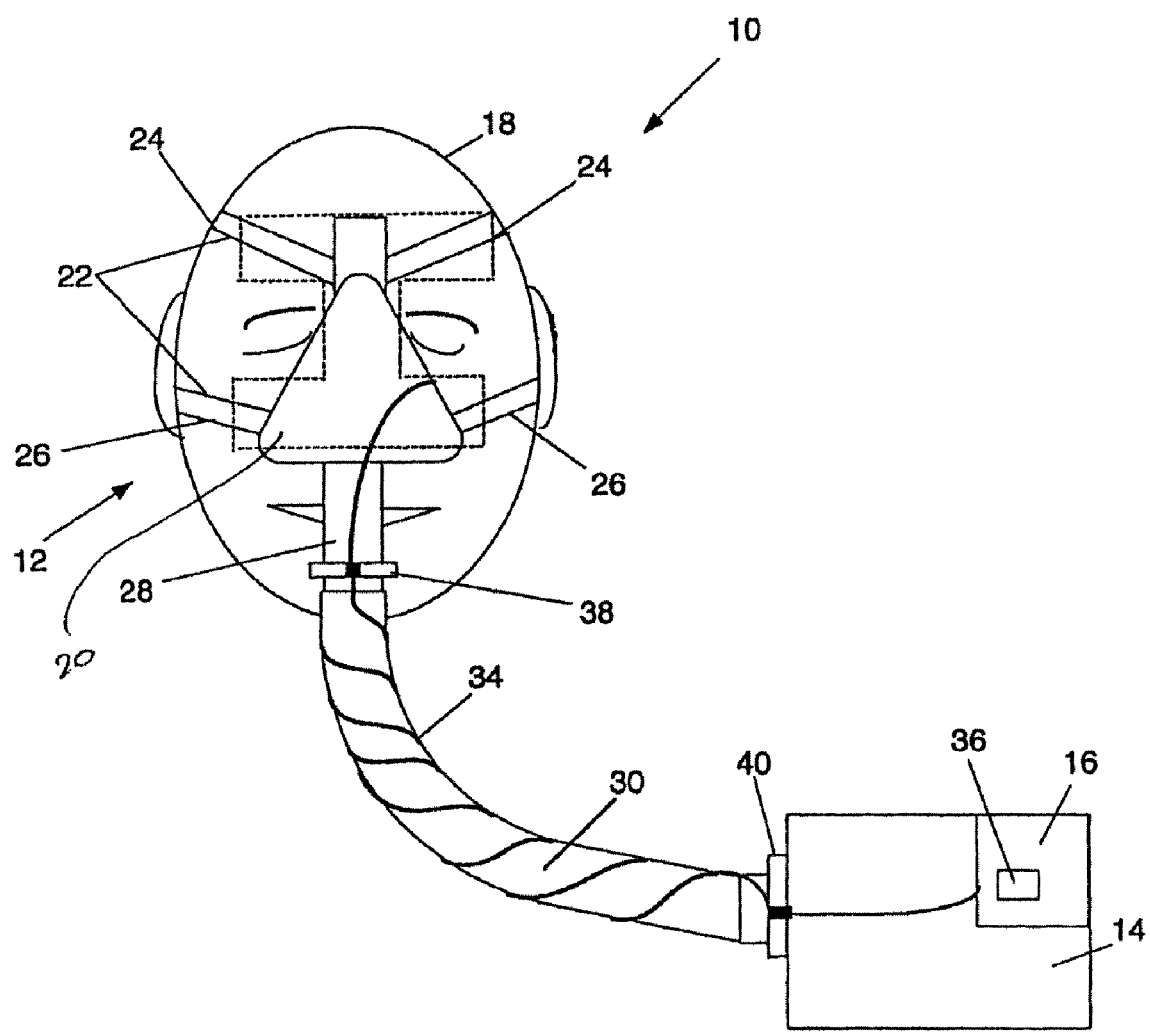
FIG. 1 is a general block diagram of a CPAP system including a mask assembly with integrated sensors in accordance with an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements. In addition, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention.

Referring now to FIG. 1, shown therein is a block diagram of a CPAP system 10 including a mask assembly 12 and a CPAP device 14 with an associated monitoring unit 16 for use by a CPAP device wearer 18. The monitoring unit 16 is shown as being an integral part of the CPAP device 14. Other configurations are possible in which the monitoring unit 16 is separate from the CPAP device 14. The mask assembly 12 includes a nasal interface or mask 20 and a harness 22. Harness 22 includes upper straps 24 and lower straps 26. The mask assembly 12 also includes a gas inlet 28 for receiving air, or another suitable gas such as pure oxygen, from the CPAP device 14 via a hose 30. The nasal mask 20 can be made from polystyrene or some other suitable material. The nasal mask 20 may also incorporate a cushion for providing a comfortable and tight fit with the face of the wearer 18.

Nasal mask 20 is one form of nasal interface that can be used with embodiments of the invention. Other forms of nasal interface are shown and described in relation to FIGS. 7 and 8.

In other embodiments, the harness may include one strap or more than two straps. Further, although the mask assembly 12 is shown having the nasal mask 20, it should be understood that the invention is also applicable to mask assemblies having a nasal/oral mask which covers both the nose and mouth of the CPAP wearer ("user"). Accordingly, the use of the word mask herein refers to both nasal masks and nasal/oral masks. The mask assembly 12 further includes sensors (e.g. electrodes E1, E2, E3, E4 and E5 of FIGS. 2a and 2b) positioned on the nasal mask 12, the straps 24 and 26 of the harness 22 or on both the nasal mask 12 and the straps 24 and 26. In this exemplary embodiment, the sensors are connected to the monitoring unit 16 via a cable 34. However, the sensors may also be wirelessly coupled to the monitoring unit 16. The sensors include electrodes for detecting one or more of the EEG, EMG or EOG of the CPAP wearer 18. The sensors may further include at least one of a blood oximetry sensor, a body position sensor and a pressure sensor as is described in further detail below.

The physiological information provided by the sensors is preprocessed by the monitoring unit 16 to improve signal quality and then processed according to a sleep efficacy algorithm 36. The sleep efficacy algorithm 36 monitors the quality of sleep for the wearer 18. This can include determining how long the wearer 18 is in a given sleep state, how many different sleep states the wearer 18 has experienced during sleep, the fragmentation of their sleep states and how many arousals the wearer 18 has experienced. Accordingly, the sleep efficacy control algorithm 36 can generate sleep profile information for the wearer 18 (the sleep profile information may include data, such as a test score, related to efficacy and compliance). The sleep efficacy algorithm 36 further generates a control signal to control the operational parameters of the CPAP device 14 such as activating or deactivating the CPAP device 14 or altering the amount of pressure that is provided to the gas inlet 28 to improve the quality of sleep of the wearer 18. The sleep efficacy algorithm 36 may use standard techniques, as is commonly known to those skilled in the art, to process the physiological signals, determine the quality of sleep and generate the control signal. The sleep efficacy algorithm 36 may identify sleep stages and generate the sleep profile information based on the physiological information sensed from the wearer 18.

The sensors are integrated directly on the inner surface of the mask assembly 12 rather than being separately attached as is done with conventional CPAP devices. Since the sensors are integrated into the mask assembly 12, the sensors do not have to be separately attached by the wearer 18. This ensures that the sensors are repeatedly applied to the same location on the wearer's face and head every time the wearer 18 wears the mask assembly 12. In addition, the mask assembly 12 can be positioned by the wearer 18, along with the sensors, without the aid of a medical professional. Furthermore, since the sensors are already in place, the preparation time prior to going to sleep is reduced for the wearer 18.

The wiring associated with the sensors is integrated into a cable 34 that runs along the length of the hose 30. The cable 34 may run along the inside or outside of the hose 30. In one embodiment, the cable 34 runs along the inside of the hose 30. In another embodiment, the cable 34 is wound around the outside of the hose 30, as illustrated in FIG. 1. In both instances, the wiring is constricted to the mask assembly 12 instead of hanging loosely on the body of the wearer 18 as is done with conventional CPAP devices. Further, the cable is shielded to reduce the possibility of receiving electromagnetic interference. Connectors 38 and 40 are also provided at either end of the hose 30 so that the hose 30 can be disconnected from the mask assembly 12 and the CPAP device 14 when the mask assembly 12 or the hose 30 requires replacement. This wiring arrangement of the invention provides the wearer 18 with increased mobility and less discomfort. Accordingly, the wearer 18 will enjoy a better quality of sleep. The mask assembly 12 with the integrated sensors is also easy to use and the sensors are automatically engaged when the wearer 18 puts on the mask assembly 12.

In the present embodiment, the electrodes that are used as sensors are preferably removably attachable to the mask assembly 12 and configured for placement against the skin of the wearer 18 for sensing the physiological signals. Accordingly, the mask assembly 12 includes attachment means (not shown) for holding the electrodes in place and providing an electrical connection with the cable 34. The implementation of the attachment means depends on the particular type of electrode that is used. For one type of electrode, the attachment means may be circular apertures, or a cutout portion, with an inner metallic contact, which may be a metallic ring. The apertures are sized to receive cylindrical electrodes which have a plastic portion, a solid conductive gel portion and a metallic conductor disposed there between. The plastic portion is placed in the aperture so that the conductive gel portion is placed against the skin of the wearer 18 when the mask assembly 12 is worn. One example of such an electrode is the Hydrodot™ biosensor, available from Physiometrix Inc. of N. Billerica, Mass., USA. These electrodes are preferable in that the electrodes require minimal preparation of the skin of the CPAP wearer 18 and the electrodes can be used for several nights before having to be replaced.

Many other types of electrodes may also be used. For instance, metal electrodes can be used which are directly integrated into the mask assembly 12 and do not have to be replaced. In this instance, the wearer 18 may be required to apply a conductive gel to each metallic electrode prior to use. The metallic electrodes may be permanently attached to the mask assembly 12 and would require cleaning each night to remove the old conductive paste before new paste is applied. Saline electrodes may also be used. Saline electrodes have a reservoir that contains saline. Over the course of the night, the reservoir empties. Accordingly, the CPAP wearer 18 must refill the reservoir prior to use of the mask assembly 12. Disk electrodes that are made from gold, silver or carbon may also be used. In addition, peel and stick electrodes that have a layer of silver-silver chloride may also be used. The peel and stick electrodes are likely to need replacement each night. One side of a peel and stick electrode has silver-silver chloride for attachment to the skin, and the other side has a conductive metallic surface. The peel and stick electrode may be held in place by a fastener that ensures that the metallic backing makes electrical contact with a corresponding wire in the mask assembly 12.

It should be noted that the type of electrodes used as the sensors does not limit the invention. Further, it should be understood that regardless of the electrodes used for the sensors, it may still be beneficial for the wearer 18 to prepare the skin locations which will receive the electrodes when the wearer 18 wears the mask assembly 12. Accordingly, the wearer 18 may cleanse and slightly abrade their skin with an appropriate cleanser such as NuPrep™ cleanser, available from Weaver & Co. of Aurora GO, USA. In some instances, the wearer 18 may also apply a conductive paste, such as EC2™ cream for example, to lower the impedance of their skin in order to obtain better physiological signals. EC2™ cream is available from Astro-Med Inc. of West Warwick, R.I., USA. The harness 22 of the mask assembly 12 may be adjusted to apply sufficient pressure to ensure that the electrodes make a good physical contact with the wearer 18.

The electrodes are preferably located at predetermined locations on the face and head of the wearer 18 in order to obtain good signal quality and different types of physiological data with a minimal number of electrodes. Due to the fewer number of electrodes, the mask assembly 12 is easier and more comfortable to wear. The inventors have been able to obtain good physiological data from as little as two electrodes which can provide EEG, EOG or EMG data. This is in contrast to standard sleep staging systems which make use of up to eleven surface electrodes located on the ears, central and occipital lobes, and besides the eyes and on the chin of the wearer. In one embodiment, the inventors have found that one set of preferred locations for the electrodes are on the nasion and approximately 4 cm higher on the forehead just above FpZ. The physiological signals obtained from the forehead at these locations provide data related to the CPAP wearer's brainwaves, facial muscle tone and eye movements. Another preferred combination includes three electrodes in which one electrode is located at the nasion, another electrode is located just above and to the left of Fp1 and another electrode is located just above and to the right of Fp2. However, other locations, and other combinations of electrodes, may also be suitable as described below.

Figure 2A:
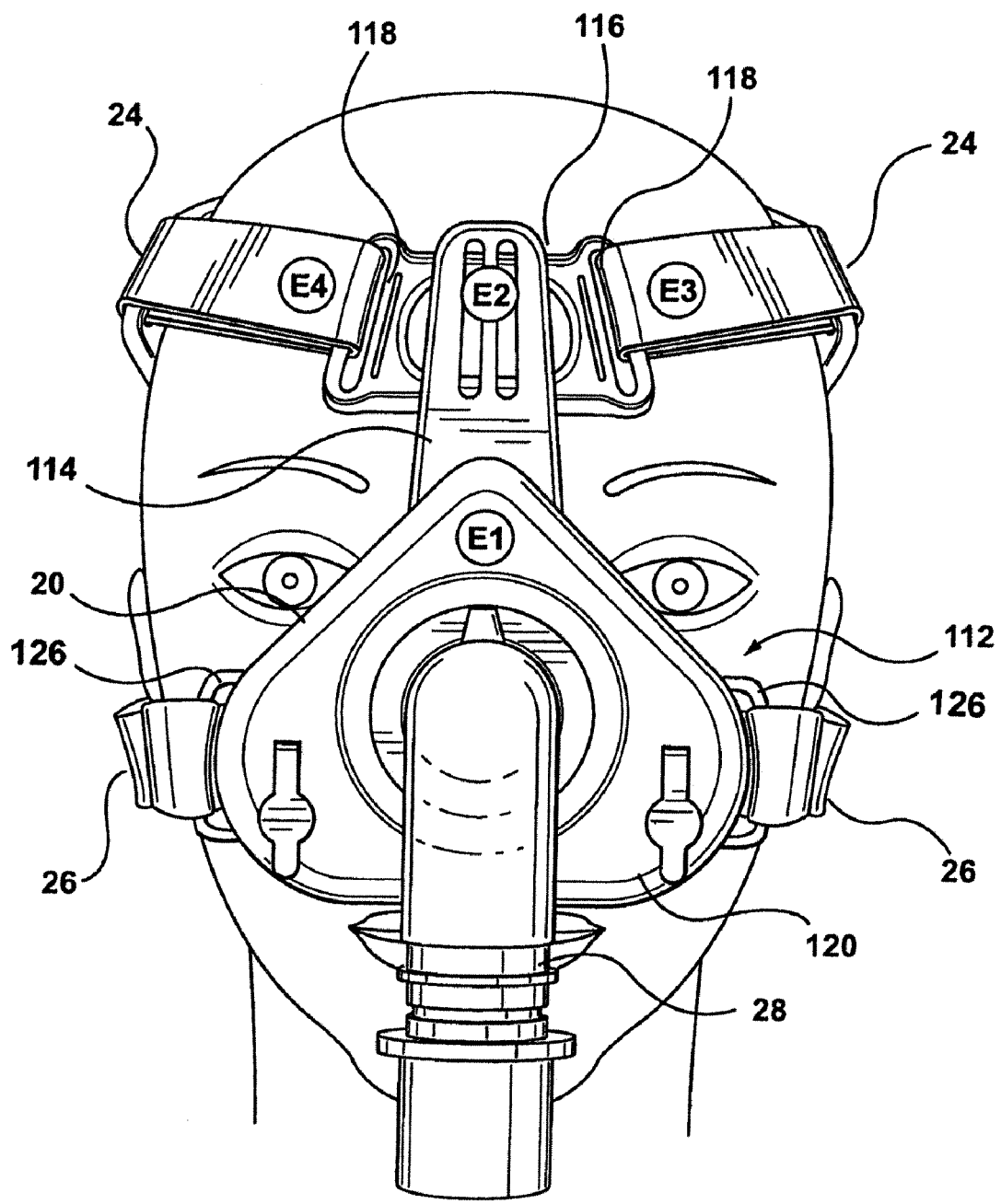
FIG. 2a is a front view of a mask assembly with integrated sensors in accordance with another embodiment of the invention.
Figure 2B:
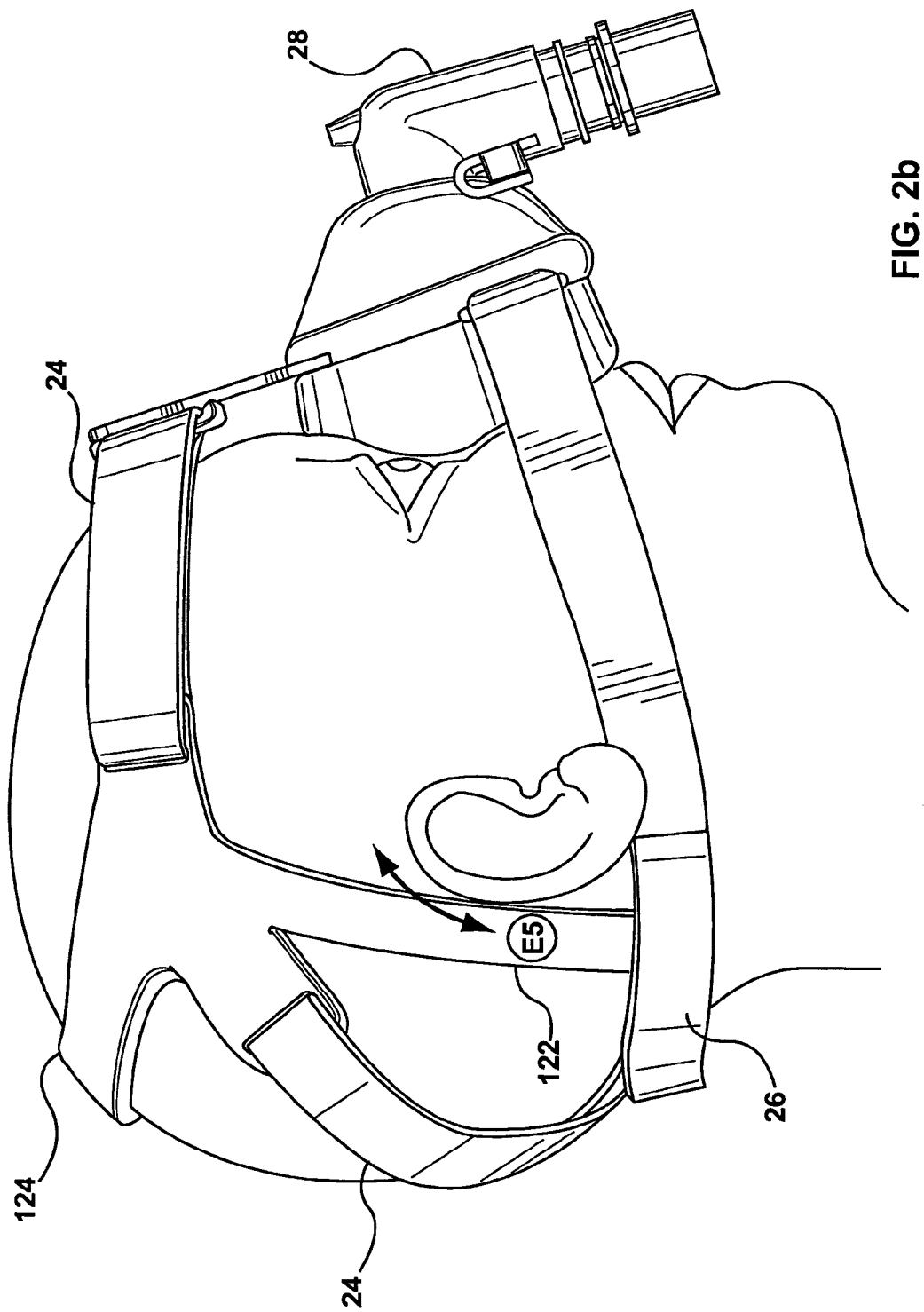

Referring now to FIGS. 2a and 2b, shown therein are front and side views, respectively, of an embodiment of the mask assembly 112 with integrated sensors in accordance with this embodiment of the invention. The nasal mask 20 of the mask assembly 112 includes a vertical mounting plate 114 that is connected to a forehead support member 116. The forehead support member 116 has two elongated apertures 118 for receiving the straps 24. The mask assembly 112 also includes a flexible seal 120 that rests against the face of the CPAP wearer 18. The seal 120 can be made from an elastomer, urethane foam, rubber or other suitable material and is glued or press fit against the rear of the nasal mask 20. The harness assembly 22 includes vertical straps 122, on either side of the head of the wearer 18, which connect the upper and lower straps 24 and 26 just behind the ear of the wearer 18. The harness assembly 22 also includes a crown strap 124 that crosses over the crown or vertex of the wearer 18 to connect the upper straps 24 to one another. There are also two elongated apertures 126 disposed at either side near the bottom of the nasal mask 20. The elongated apertures 126 are engaged by the lower straps 26 of the harness assembly 22.

In this embodiment, exemplary locations are shown for electrodes E1, E2, E3, E4 and E5. Electrodes E1 and E2 are located on the nasal mask 20 and the vertical mounting plate 114 that correspond to the nasion and central forehead regions, respectively, of the CPAP wearer 18. Electrodes E3 and E4 are located on the right and left upper straps 24. Electrode E5 is located on the mastoid of the CPAP wearer 18.

The electrode E5 may be placed anywhere behind the right or left ear of the wearer 18. The wires from the electrodes E1, E2, E3, E4 and E5 are not shown. However, it should be understood that separate wires from each electrode E1, E2, E3, E4 and E5 are bundled together into the cable 34 and run along the hose 30 of the CPAP system 10 as described above.

The electrode E1 is located at, or approximately 1 cm above, the nasion, which is the depression at the root of the nose of the wearer 18, and is roughly between the eyebrows of the wearer 18. The electrodes E3 and E4 are located just below the hairline and spaced apart lining up between the centerline and the outside of the eyes of the wearer 18. The horizontal and vertical displacements of electrodes E3 and E4 are important for detecting certain EEG information as described below. For instance, if the electrodes E3 and E4 are too close together, then they will not be able to distinguish signals that originate from the deeper structures of the brain. The electrode E5 on the mastoid can help to detect alpha waves in the EEG of the wearer 18 since the electrode E5 is close to the occipital region of the wearer 18. Physiological information from the electrode E5 may be necessary if sufficient information cannot be detected from the frontal electrodes (this depends on the quality of sleep staging performed by the efficacy monitoring algorithm 36).

Electrode locations other than those shown for electrodes E1, E2, E3, E4 and E5 are also possible. For instance it is possible to place one electrode below and beside one eye of the CPAP wearer 18 and the other electrode above and beside the other eye of the CPAP wearer 18. This is the traditional location of EOG electrodes which maximally detect horizontal and vertical eye movements. In addition, it may be possible to vertically flip the location of the electrode E1 with respect to the electrodes E3 and E4. Therefore, rather than forming an upside triangle pattern, as shown in FIG. 2a, the electrodes E1 E3 and E4 can be oriented in a right side up triangle pattern. This may involve elongating the vertical mounting plate 114.

It is to be noted that each of these electrode locations are on exposed skin surfaces (i.e. not on top of hair) in order to provide a good skin-electrode contact as well as to provide minimal discomfort to the wearer 18. Further, the electrodes are preferably not placed on any large muscles to prevent having the physiological data contaminated with undesirable muscular artifacts. Further, the degree to which the locations of the electrodes E1, E2, E3, E4 and E5 can vary depends on the nature of the efficacy monitoring algorithm 36. Small changes on the order of +/−1 cm have little effect. However, it is important to maintain a certain amount of vertical displacement between electrode E1 and the other frontal electrodes E2, E3 and E4. A vertical displacement of as much as 6 cm may be used.

Various subsets of the electrodes may be used in particular embodiments of the invention. One combination may be electrodes E1 and E2. Another combination may be electrodes E1, E3 and E4. Another combination may be electrodes E3, E4 and E5. Another combination may be electrodes E2 and E5. In each of these combinations, there is no reference electrode since one of the electrodes is used to provide both ground and reference signals. This results in a sight reduction in signal quality but the benefit is a reduced number of electrodes. Alternatively, it may be possible to use one of the electrodes as a ground electrode and another of the electrodes as a reference electrode, if necessary. For example, in one combination, electrode E2 may be used to provide a ground signal and electrode E1 may be used to provide the reference signal.

A single channel of physiological information can be derived from two frontal electrodes. However, there is a reduction in the amount of physiological information that is available to determine the sleep stages when only a single channel is used. For instance, with a single channel, detection of eye movements is limited, and EMG information is weak. Also standard EEG features such as sawtooth waveforms, spindles, K-complex, alpha and delta waveforms may be changed. Furthermore, it is difficult to resolve K-complex signals and spindles from one another using only the electrodes E4 and E3. These signals are more difficult to detect because they do not originate in the frontal lobes of the brain. However, they are useful since they can be used to differentiate between some of the sleep stages. Accordingly, it is preferable, and more robust, although not necessary, to use a subset of electrodes that contains at least three electrodes. However, in some cases it may be possible to use only two electrodes.

The combination of electrodes E1, E3 and E4 provides three channels of physiological data which have a sufficient content of EEG, EMG and EOG information to perform frontal sleep staging (the term "front" is used since the physiological data is obtained from the front/face of the wearer 18). One of the three channels is obtained from electrode pair E3 and E1, another of the other channels is obtained from electrode pair E4 and E1 and another of the channels is obtained from electrode pair E3 and E4. The data provided by electrode pairs E3 and E1, and E4 and E1 may be used to detect EEG and EOG signals while the data provided by electrode pair E3 and E4 may be used to detect EMG signals. Accordingly, the electrode configuration of electrodes E1, E3 and E4 may be used to detect both horizontal and vertically oriented potentials which is desirable for detecting horizontal and vertical eye movements. Also, dipoles in the brain generate EEG spindles that have different orientations. These EEG spindles, which are helpful for sleep staging, can be detected with electrodes that detect horizontal and vertically oriented potentials. Two channels are also better than a single channel in distinguishing eye blinks from other EEG waveforms such as K-complex delta activity that is usually less symmetric. With this electrode configuration, eye blinks and rapid eye movements can be used to assist in the detection of wake and REM states since alpha frequencies, which also indicate sleep arousal, originate in the occipital lobe at the rear of the head of the wearer 18 and this is difficult to detect with frontal electrodes. Arousals are also determined by an abrupt increase in alpha and beta band activity of the EEG signals which is evident on the frontal channels. Arousals are important for determining the quality of sleep and the efficacy of therapy.

Figure 3:
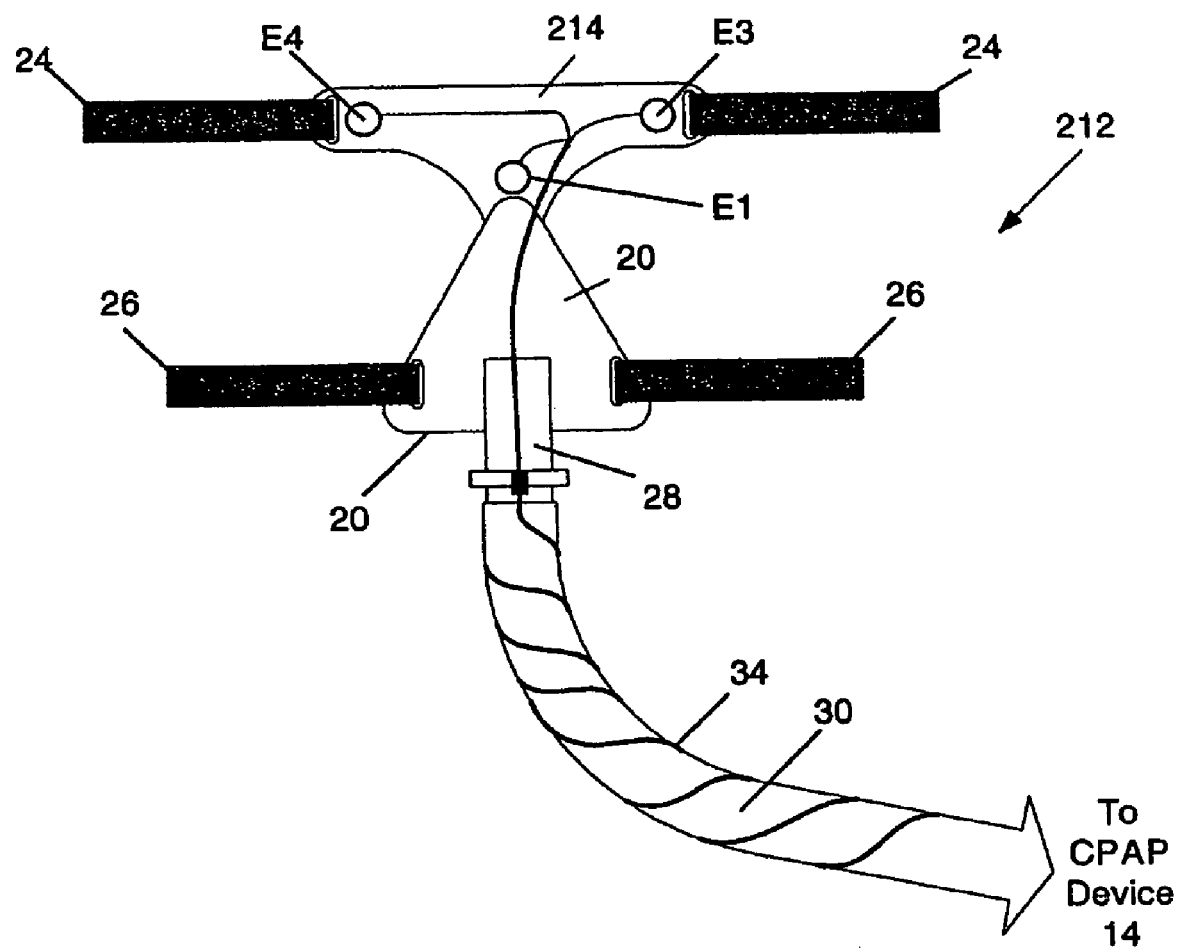
FIG. 3 is a front view of mask assembly with integrated sensors according to an alternate embodiment.

Referring now to FIG. 3, shown therein is a front view of an alternate embodiment of a mask assembly 212 with integrated sensors in accordance with the invention. In this embodiment, the nasal mask 20 includes a contoured forehead support member 214 with horizontal sides that extend over the eyebrows of the wearer 18. The electrodes E1, E4 and E3 are all integrated onto the forehead support member 214 of the nasal mask 20 rather than the left and right straps 24. In particular, the electrode E1 is preferably located at the nasion of the wearer 18, the electrode E3 is located near the right horizontal end of the forehead support member 214 horizontally offset with respect to the center of the right eye of the wearer 18, and the electrode E4 is located near the left horizontal end of the forehead support member 214 horizontally offset with respect to the center of the left eye of the wearer 18. Electrodes E3 and E4 preferably rest just below the hairline of the wearer 18.

Figure 4:
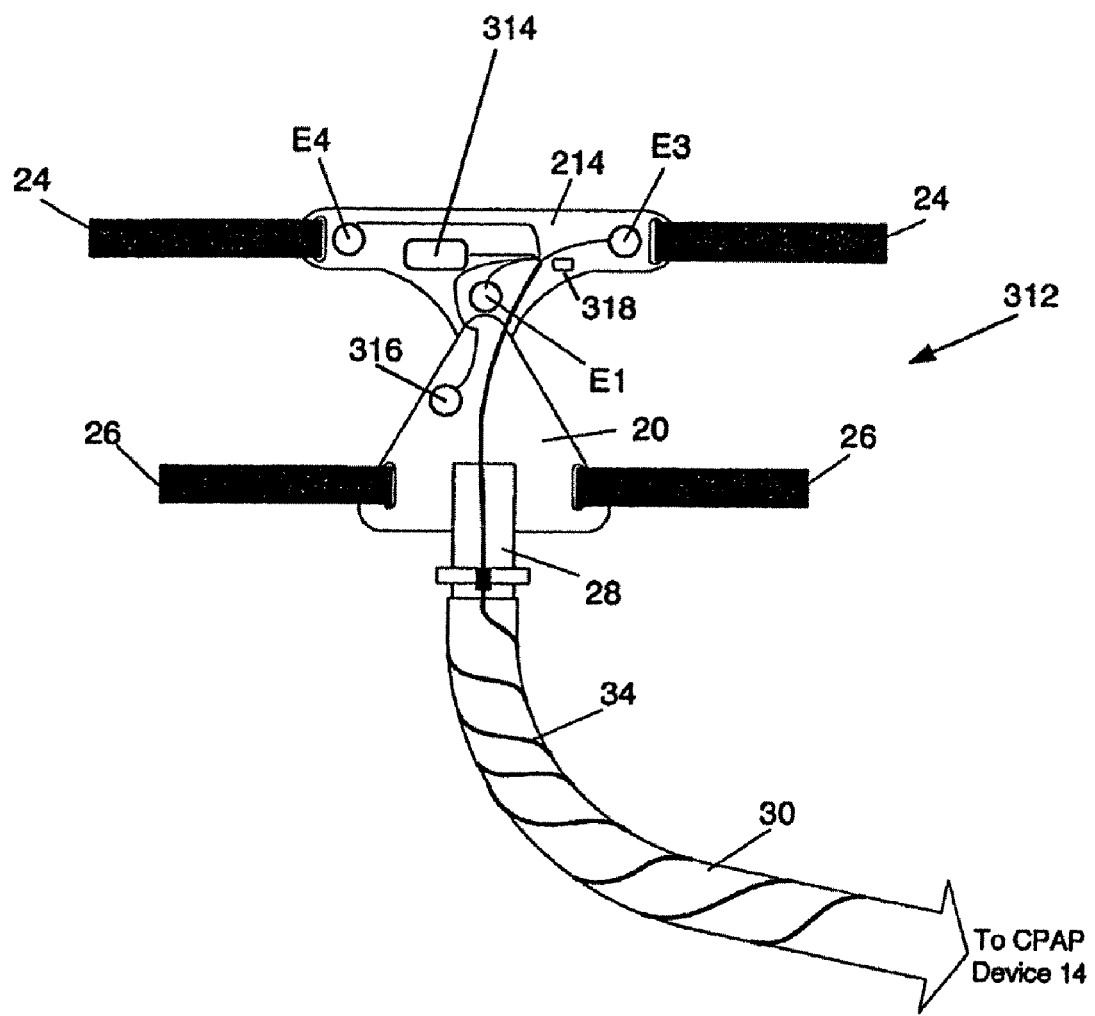
FIG. 4 is a front view of a mask assembly with integrated sensors according to another embodiment.

Referring now to FIG. 4, shown therein is a front view of another alternate embodiment of a mask assembly 312 with additional integrated sensors in accordance with the invention. The mask assembly 312 includes an oximeter sensor 314, a pressure transducer 316 and a position sensor 318. It should be noted that not all three additional sensors 314, 316 and 318 are needed and that additional embodiments are possible in which various subsets of these additional sensors are integrated into the mask assembly 312. The oximeter sensor 314 is preferably located at the forehead support member 214 in close proximity with the forehead of the wearer 18. Alternatively, the oximeter sensor 314 may be located on an ear clip or inserted into the ear canal and a wire run from the oximeter sensor 314 along one of the straps 24 or 26 and along the nasal mask 20 at which point the wire is integrated within the cable 34. The pressure transducer 316 is disposed within the nasal mask 20 preferably in close proximity to the gas inlet 28. The position sensor 318 is also preferably located on the forehead support member 214. However, the position sensor 318 may be located within the nasal mask 20; no contact with the skin is required and so the location of the position sensor 318 may be whatever is best suits the ergonomics and manufacturability of the mask assembly 12.

The oximeter sensor 314 may be used to help detect sleep apnea since it provides physiological information from which desaturation and resaturation events in oxygen saturation of the arterial blood of the wearer 18 can be identified. During sleep apnea, there is no air movement into the chest of the wearer 18 and the wearer 18 becomes progressively more hypoxic and hypercarbic. Consequently, OSA may be detected by looking at the rate of change of oxygen desaturations measured during sleep. The oximeter sensor 314 includes light emitting diodes that emit near infrared light at the forehead skin of the wearer 18. The light gets scattered and a portion of the light is reflected to the oximeter sensor 314. The amount of light that gets reflected is related to the spectral absorption of the underlying tissue from which the average oxygenation of the tissue can be derived. Conventional forehead reflectance oximeters may be used, such as the one by Masimo of Irving, Calif., USA to measure peripheral blood oxygenation. Also, the INVOS™ cerebral oximeter made by Somanetics of Troy, Mich., USA may be used as the oximeter sensor 314 to measure oxygenation of the brain.

The pressure transducer 316 is used to detect the pressure within the cavity of the nasal mask 20 from which the breathing rate of the wearer 18 can be derived. The breathing rate of the wearer 18 can provide an indication of apnea and hypopnea events. Any suitable pressure transducer with an appropriate size may be used.

The position sensor 318 is used to detect the position of the head of the CPAP wearer 18. This is important since the occlusion that occurs during sleep apnea happens mainly when the wearer 18 is lying on their back since the soft tissue in the back of the throat collapsing due to gravity. In addition, when the wearer 18 is in the supine position, more effort is required to breathe and consequently additional pressure from the CPAP device 14 is needed. The position of the head relates closely to that of the throat. Accordingly, locating the position sensor 318 on the mask assembly 12 is advantageous. In an alternative, it may be possible to locate a position sensor on the chest of the wearer 18 and run the corresponding wire up to the mask assembly 12 where it is integrated into the cable 34.

Figure 5A:
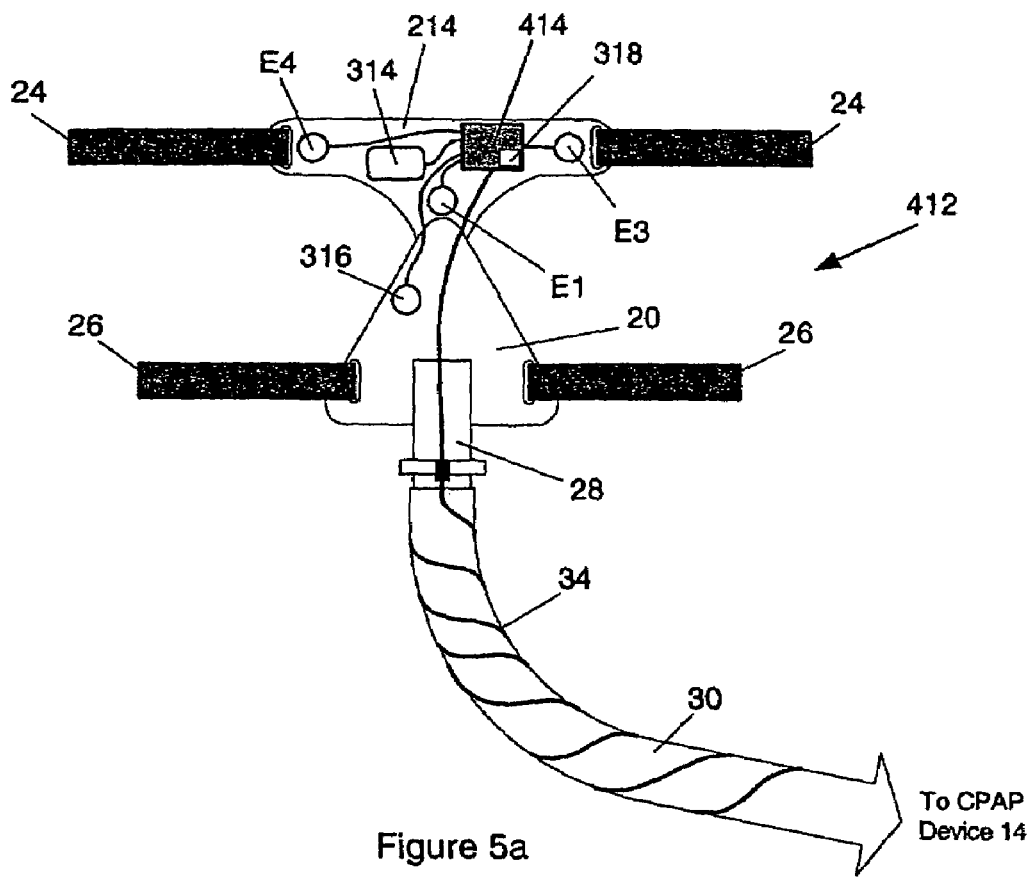
FIG. 5a is a front view of a mask assembly with integrated sensors and a remote processing unit according to another embodiment.

Referring now to FIG. 5a, shown therein is a front view of another embodiment of a mask assembly 412 with integrated sensors and a remote processing unit 414 in accordance with the invention. The electrodes E1, E3 and E4, the oximeter sensor 314, the pressure transducer 316 and the position sensor 318 are connected to the remote processing unit 414 which processes the signals provided by these sensors prior to transmitting the signals to the monitoring unit 16 via the cable 34. This results in better quality signals with reduced noise and less contamination caused by motion and electromagnetic interference. The cable 34 may include a power supply connection to provide power to the remote processing unit 414. Alternatively, the remote processing unit 414 may be battery powered. It should be understood that for this embodiment there can be various combinations of the sensors since the oximeter sensor 314, the pressure transducer 316 and the position sensor 318 are optional.

Figure 5B:
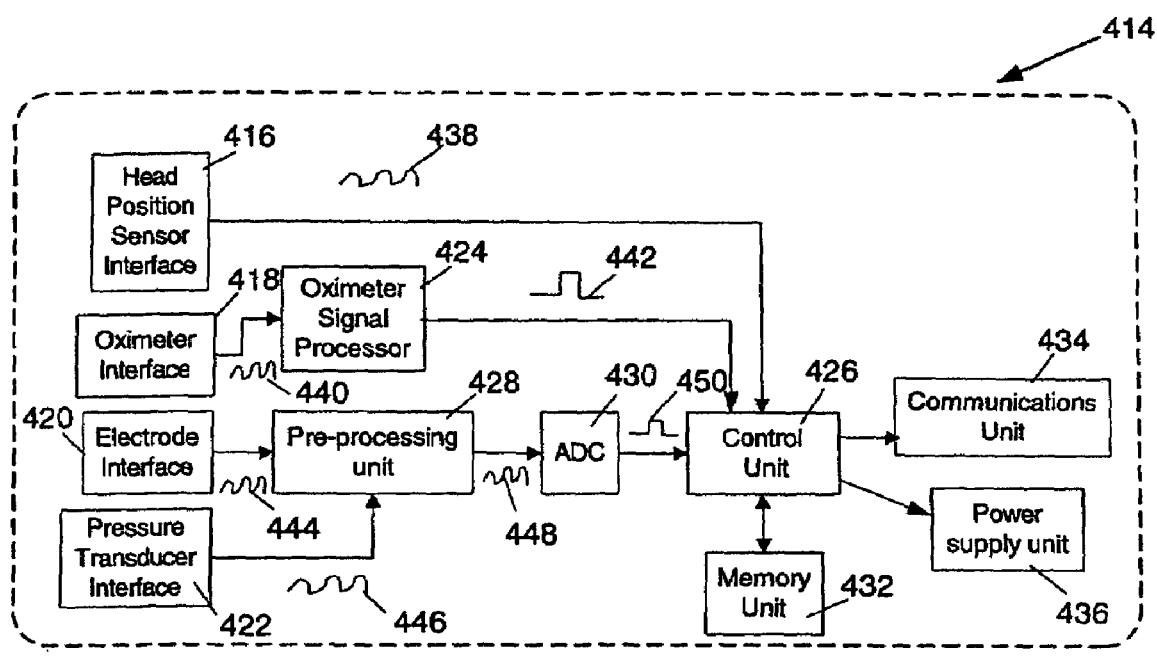

Referring now to FIG. 5b, shown therein is a block diagram of the remote processing unit 414. The remote processing unit 414 includes several interfaces for providing an electrical connection with the integrated sensors on the mask assembly 412. The remote processing unit 414 includes a head position sensor interface 416, an oximeter interface 418, an electrode interface 420 and a pressure transducer interface 422 for electrical interface with the appropriate sensor. As mentioned previously, some of the sensors are optional. Accordingly, the remote processing unit 414 may not require each of the interfaces shown in FIG. 5b.

The remote processing unit 414 further includes an oximeter signal processor 424 that is connected to the oximeter interface 418 and a control unit 426. The control unit 426 directs the activity of the remote processing unit 414 and processes each of the signals provided by the sensors. The control unit 426 may be a digital signal processor. It should be noted that the oximeter signal processor 424 is optional and the processing performed by the oximeter signal processor 424 may be done by the control unit 426.

The remote processing unit 414 further includes a pre-processing unit 428 that is connected to the electrode interface 420 and an analog-to-digital converter (ADC) 430 that is connected between the pre-processing unit 428 and the control unit 426. It is well known to those skilled in the art that the EEG, EMG and EOG signals are very small amplitude signals (on the order of micro-volts) and that pre-processing is required to remove noise from these signals and amplify these signals. Accordingly, the pre-processing block 428 includes a high-pass filter stage with a cutoff frequency of 0.1 to 1 Hz for removing large DC contact potentials and an amplification stage with a gain on the order of 1,000 V/V for amplifying the electrode signals.

The remote processing unit 414 further includes a memory unit 432 connected to the control unit 426 for storing the measured signals. The memory unit 432 may also be used for storing operational parameters for the remote processing unit 414 as well as programs that are used to process the measured signals. The memory unit 432 is non-volatile and can be a flash memory unit, and the like.

The remote processing unit 414 also includes a host communications unit 434 and a power supply unit 436 connected to the control unit 426. The communications unit 434 directs communication between the remote processing unit 414 and the monitoring unit 16. The communications unit 434 may be a high speed, synchronous serial port such as a UART and the like. The power supply unit 434 is connected to the power wire provided by the cable 34 and processes the power supply signal for use by the remote processing unit 414. The processed power supply signal is provided to the control unit 426 to power the control unit 426 and for distribution to the remaining components of the remote processing unit 426.

It should be noted that the remote processing unit 414 is optional and that all of the signal processing that is done by the remote processing unit 414 may be done by the monitoring unit 16. In this case, the monitoring unit 16 has similar components as those shown in FIG. 5b.

In use, the head position interface 416 receives a position signal 438 that is provided by the position interface sensor 318 (position sensors based on mercury switches provide digital signals). The oximeter interface 418 receives a raw oximetry signal 440 from the oximeter sensor 314. The oximeter signal processor 424 processes the raw oximeter signal 440 and provides a processed oximetry signal 442. The electrode interface 420 receives raw electrode signals 444 from the electrodes E1, E3 and E4 and the pressure transducer interface 450 receives a raw pressure signal 446. Both of these raw signals are sent to the pre-processing unit 428 which generates pre-processed signals 448. The pre-processed signals 448 are then digitized by the ADC 430 resulting in digital pre-processed signals 450. The position signal 438, processed oximetry signal 442 and digital pre-processed signals 450 are then sent to the control unit 426.

In an alternative, the remote processing unit 414 may also perform the sleep efficacy algorithm 36 which can be stored on the memory unit 432. Accordingly, the remote processing unit 414 may determine the sleep profile information for the wearer 18, generate the control signal to improve the sleep quality experienced by the wearer 18 and send the control signal to the CPAP device 14 to augment the pressure that is delivered to the nasal mask 20. In addition, the sleep profile information may be transmitted to a caregiver through a wire connection to a computer. Wireless transmission may also be used as discussed below. The sleep efficacy algorithm 26 may employ a frontal staging algorithm to calculate the sleep profile of the CPAP wearer 18.

Figure 5C:
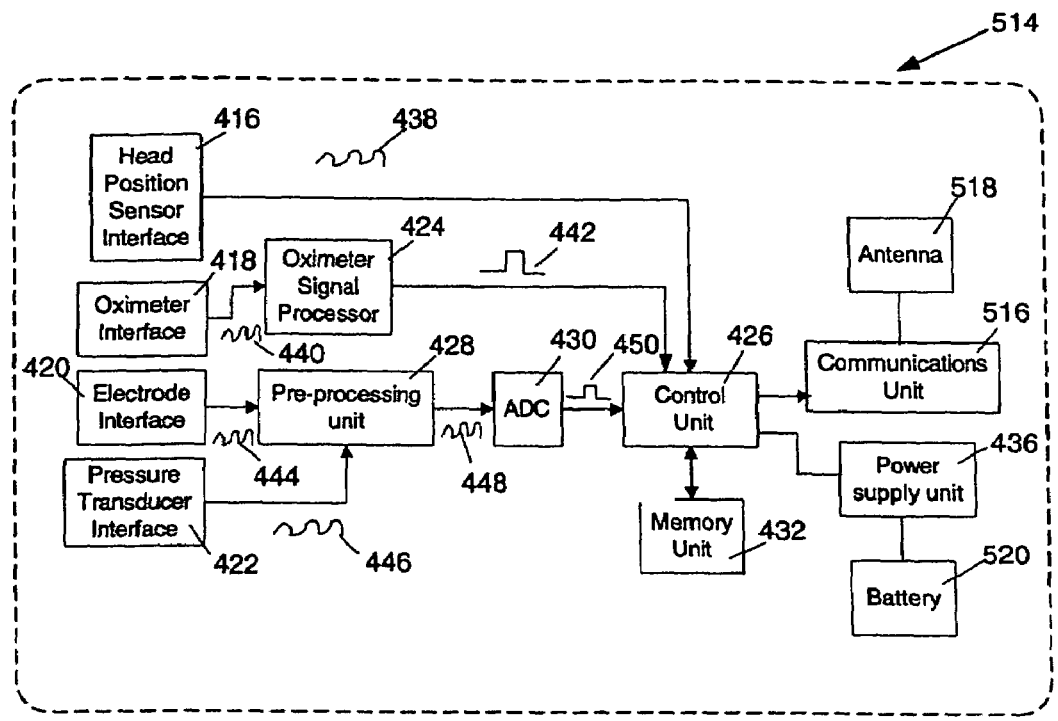
FIG. 5c is a block diagram of the remote processing unit incorporating a wireless communication according to another embodiment.

Referring now to FIG. 5c, shown therein is a block diagram of an alternate embodiment of a remote processing unit 514 incorporating a wireless communications unit 516 and an antenna 518 in accordance with the invention. The wireless communication unit 516 runs a suitable wireless protocol such as the BLUETOOTH™ protocol which is suitable for short-range communication. For longer-range communication, the wireless communication unit 516 may employ another communications protocol such as CDMA. The remote processing unit 514 also includes a battery 520 that is connected to the power supply unit 436. Accordingly, in this case, there is no need for the cable 34.

For the remote processing units 412 and 512, noise is dealt with by selecting amplifiers with a high CMRR, by having low capacitance isolation of the power supply unit 436 and having a low impedance connection from the electrodes to the skin of the wearer 18. It should be understood that the embodiments for remote processing unit 412 and 512 are exemplary and that some of the components may be combined. For instance, the memory unit 432 and the communications unit 434 may be integrated into the control unit 426.

Figure 6:
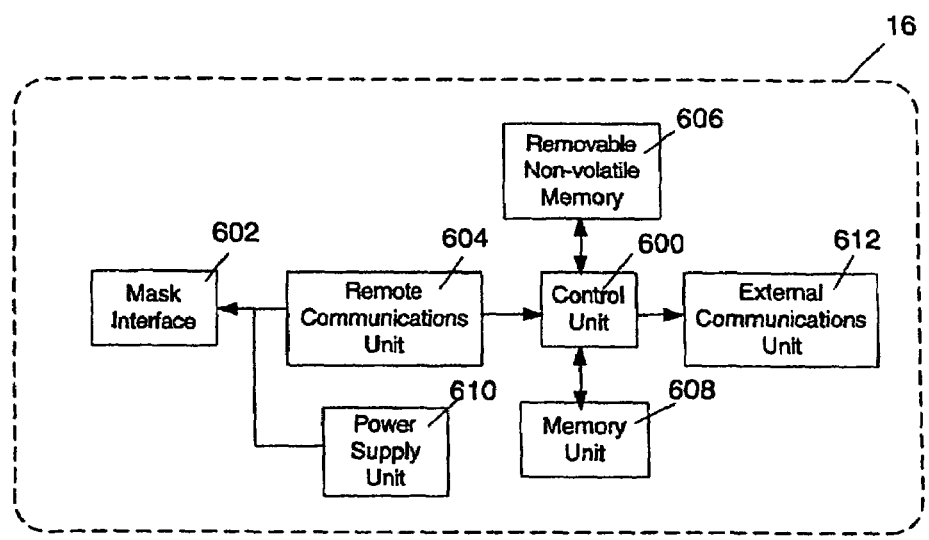
FIG. 6 is a block diagram of the monitoring unit of FIG. 1 in accordance with another embodiment.

Referring now to FIG. 6, shown therein is a block diagram of an exemplary embodiment of the monitoring unit 16 of FIG. 1. The monitoring unit 16 may be directly integrated within the CPAP device 14 or it may be separate and works alongside the CPAP device 14. The monitoring unit 16 includes a control unit 600, a mask interface 602, a remote communications unit 604, a removable non-volatile memory 606, a memory unit 608, a power supply unit 610 and an external communications unit 612 connected as shown in FIG. 6.

The control unit 600 controls the operation of the monitoring unit 16 and may be a digital signal processor, a controller or the like. The mask interface 602 is an interface between the monitoring unit 16 and the sensors on the mask assembly. Accordingly, the mask interface 602 may be an electrical interface with appropriate terminals for receiving the cable 34. Alternatively, in the instances in which the mask assembly includes a wireless remote processing unit, the mask interface 602 may be an antenna. The remote communications unit 604 directs the transmission of data between the mask assembly and the monitoring unit 16. In the instance in which the mask assembly includes a wireless remote processing unit, the remote communications unit 604 employs an appropriate communications protocol such as the BLUETOOTH™ protocol. In the case of a wired connection to the mask, the remote communications unit 604 may be a high speed, synchronous serial port such as a UART and the like.

The control unit 600 receives the data transmitted from the mask assembly. In one embodiment, the control unit 600 may execute the sleep efficacy algorithm 36, which is stored in the memory unit 608, and generate a control signal for the CPAP device 14. In another embodiment, the remote processing unit may perform the sleep efficacy algorithm 36, generate the control signal and send the control signal, as well as the sleep profile information, to the control unit 600. In both cases, the control unit 600 sends the control signal to the CPAP device 14 via the external communications unit 612. The external communications unit 612 may also be used to connect to an external computer or network for transfer of the sleep profile information. Accordingly, besides having a connection to the CPAP device 14, the external communications unit 612 may include an Ethernet device, a USB device, a telephone or wireless modem and the like for connection to an external computing device or network.

The removable non-volatile memory 606 may store the sleep profile information that includes data, such as test scores, related to the compliance and efficacy of CPAP therapy on the wearer 18. The removable non-volatile memory 606 may also store raw data obtained from the sensors on the mask assembly for inspection by a qualified health professional. The removable non-volatile memory 606 is optional and all of this data may be stored on the memory unit 608.

As mentioned previously, the sleep efficacy algorithm 36 may use a frontal staging algorithm, based on at least the electrode signals, to determine which stage of sleep the wearer 18 is in. The information provided by the electrodes is important since it is well known that some sleep apnea events occur more frequently in some of the sleep stages rather than others. The sleep stages include sleep stages 1, 2, 3 and 4 and REM sleep. In some individuals, sleep apnea may be more prevalent in the REM stage. In stage 1 sleep, the EEG is characterized by low voltage, mixed frequency activity, without rapid eye movement and usually with relatively high EMG activity. Stage 2 sleep is characterized by sleep spindles, which are bursts of distinctive waves of 12 to 14 Hz predominantly seen in the central vertex region, as well as K complexes which are delineated, negative, sharp waves immediately followed by positive components lasting more than 0.5 seconds. The K complexes predominantly appear in the central vertex region. REM sleep is characterized by low voltage, mixed frequency EEG activity with the lowest EMG activity and sawtooth waves that appear in the frontal regions of the brain usually in conjunction with bursts of rapid eye movements. Muscle atonia occurs during REM sleep which can affect airway patency and result in increased sleep apnea. In addition, sleep onset can be determined by the alpha EEG waveform as well as eye blinks (i.e. the lack thereof). Sleep stages 3 and 4 are known as deep sleep states. They are characterized by the dominance of high amplitude (for example, greater than 75 µV) and low frequency (for example, 0.5 to 2 Hz) slow delta activities. Delta activities are predominantly seen in the frontal region. Accordingly, electrode position is important for detecting each of these types of signals.

In one instance, the sleep efficacy algorithm 36 activates the CPAP device 14 only once the CPAP wearer 18 falls asleep, thereby easing the transition from wake to sleep, making the therapy more comfortable and improving compliance. The sleep efficacy algorithm 36 may also use the sleep profile information to vary the CPAP titration pressure depending on the sleep stage. For example, more pressure may be delivered in the REM sleep stage in which the incidence of sleep apnea increases due to the relaxation of the throat muscles.

When combined with an automated sleep efficacy algorithm that performs sleep staging and pressure control, the mask assembly of the invention provides a quick, convenient means for monitoring and improving the sleep profile of the wearer 18. The sleep profile information can be used by physicians to improve the quality of care and allow them to objectively assess the efficacy of treatment and monitor changes to therapy. The efficacy of therapy can be used by employers or law enforcement personnel to prevent hazardous equipment such as cars, airplanes and industrial machines from being operated by individuals who are impaired due to inadequate sleep. The efficacy of therapy can also be used by insurers to determine the need for continued treatment in order to save costs. Further, the sleep profile information can be used to control CPAP therapy.

Figure 7:
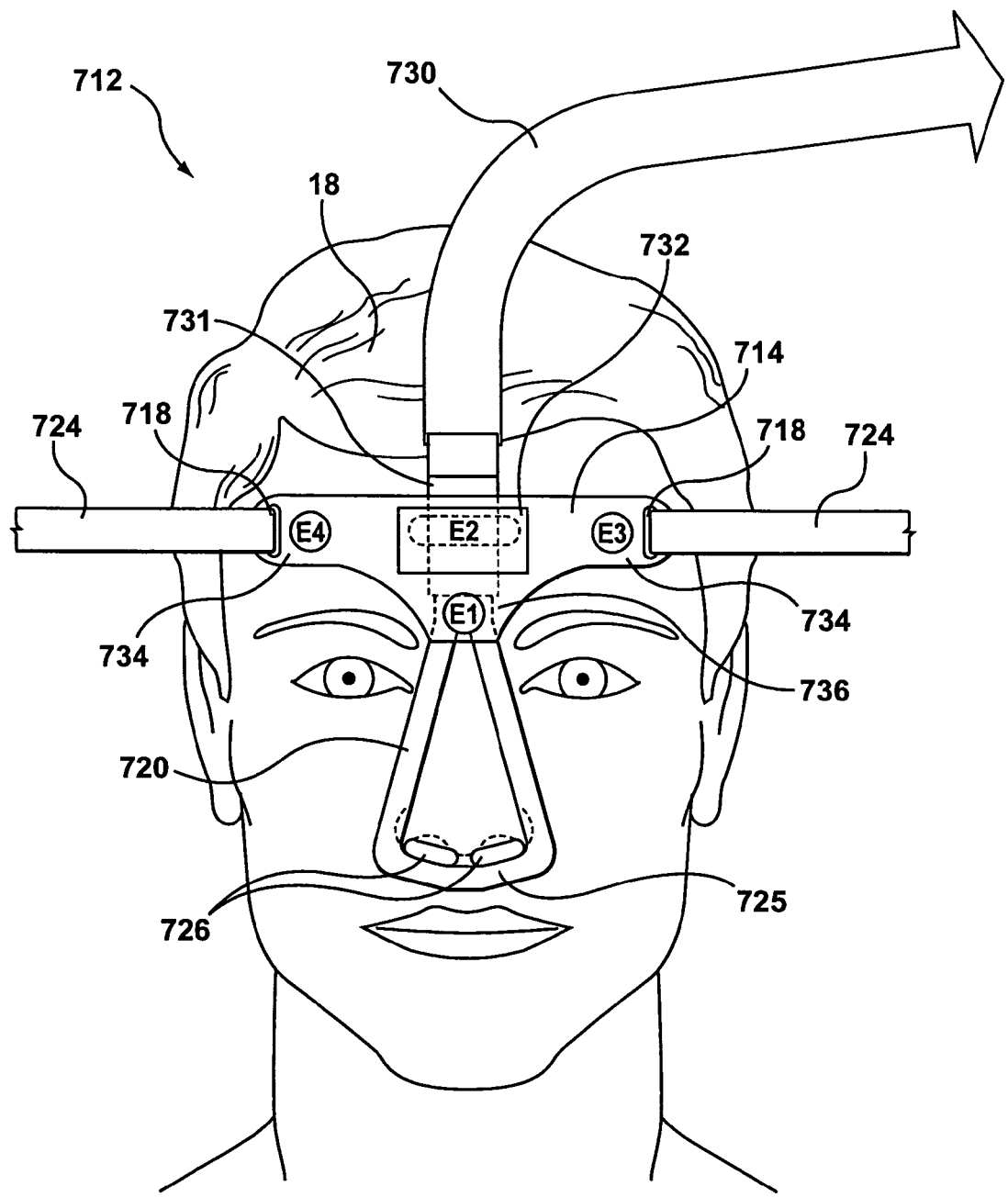
FIG. 7 is a front view of a mask assembly according to another embodiment.

Referring now to FIG. 7, there is shown an alternative mask assembly 712. The mask assembly 712 comprises a flexible forehead plate 714 for holding electrodes E1, E2, E3 and E4 in position on the forehead of the wearer 18 and a strap 724 for securing the forehead plate 714 to the wearer 18. Mask assembly 712 also comprises a nasal interface 720 connected to forehead plate 714 via connector member 732. Nasal interface 720 receives pressurized gas through a gas supply tube 730 for feeding the gas directly into the nostrils of the wearer 18 through gas outlet ports 726 of nasal interface 720.

Nasal interface 720 is shown in FIG. 7 as being shaped as a loop extending downwardly over the wearer's face from the forehead and diverging around the nose. The divergent limbs of the loop of nasal interface 720 are joined at the bottom by a lip portion 725 which is designed to generally overlie the upper lip of the wearer 18 and be held upwardly against the wearer's nose so that outlet ports 726 feed directly into the nostrils of the wearer 18. Outlet ports 726 may be formed as tubular extensions which extend well into the wearers nostrils or may be formed so as to otherwise substantially occlude the wearer's nostrils so that relatively little of the gas supplied through gas outlets 726 leaks out of the nostrils.

Forehead plate 714 is formed roughly in a T-shape when viewed from the front while worn by the wearer 18. A lower portion 736 projects downwardly from forehead plate 714 and houses electrode E1 so as to generally, or at least partly, overlie the nasion area of the wearer 18. Electrodes E2, E3 and E4 are spaced laterally across forehead plate 714 in a similar manner to the arrangement shown in FIG. 2A. Electrode E2 acts as a ground electrode relative to the measured signals from electrodes E1, E3 and E4. Electrode E3 and E4 are positioned in laterally extending wings 734 of forehead plate 714 so as to overlie a central part of the forehead on each lateral side in a similar manner to the arrangements shown and described in relation to FIG. 2A.

Nasal interface 720 is connected to forehead plate 714 by connector 732 at a tubing portion 731 which extends between the nasal loop of nasal interface 720 and gas supply tube 730. The connection achieved by connector 732 may be mechanical or chemical, for example by snap fitting or adhesion. Other forms of removable or non-removable connection may be provided by connector 732.

Strap 724 is connected to forehead plate 714 at each lateral wing 734 by any suitable attachment mechanism. As shown in FIG. 7, strap 724 is attached to forehead plate 714 by looping through a suitably shaped slot 718 in each lateral wing 734. Strap 724 passes around the head of wearer 18 and attaches to itself to form a loop snugly fitting around the wearer's head. The attachment of the parts of strap 724 together may be achieved by any suitable attachment mechanism.

Although not specifically shown in FIG. 7, forehead plate 714 may comprise additional sensors, such as those shown and described in relation to other embodiments. Additionally, the features of mask assembly 712 may be combined with, or substituted for, other features of other mask assembly embodiments shown and described herein, where such combination or substitution would result in a workable mask assembly. Features described in relation to other embodiments may be used instead of, or in addition to, the features of mask assembly 712, where such addition or substitution of features would result in a workable mask assembly.

As with other embodiments of the mask assembly, electrodes E1, E2, E3 and E4, as well as any other sensors located on forehead plate 714, may employ a wireless communication module to communicate with monitoring unit 16. Such a wireless communication arrangement is shown and described in co-pending U.S. patent application Ser. No. 11/130,221, filed on May 17, 2005 and entitled "Wireless Physiological Monitoring System" the entire contents of which is hereby incorporated by reference. Alternatively, dedicated conductors may be connected to each such electrode or sensor and wired back to monitoring unit 16, for example along gas supply tube 730.

Figure 8:
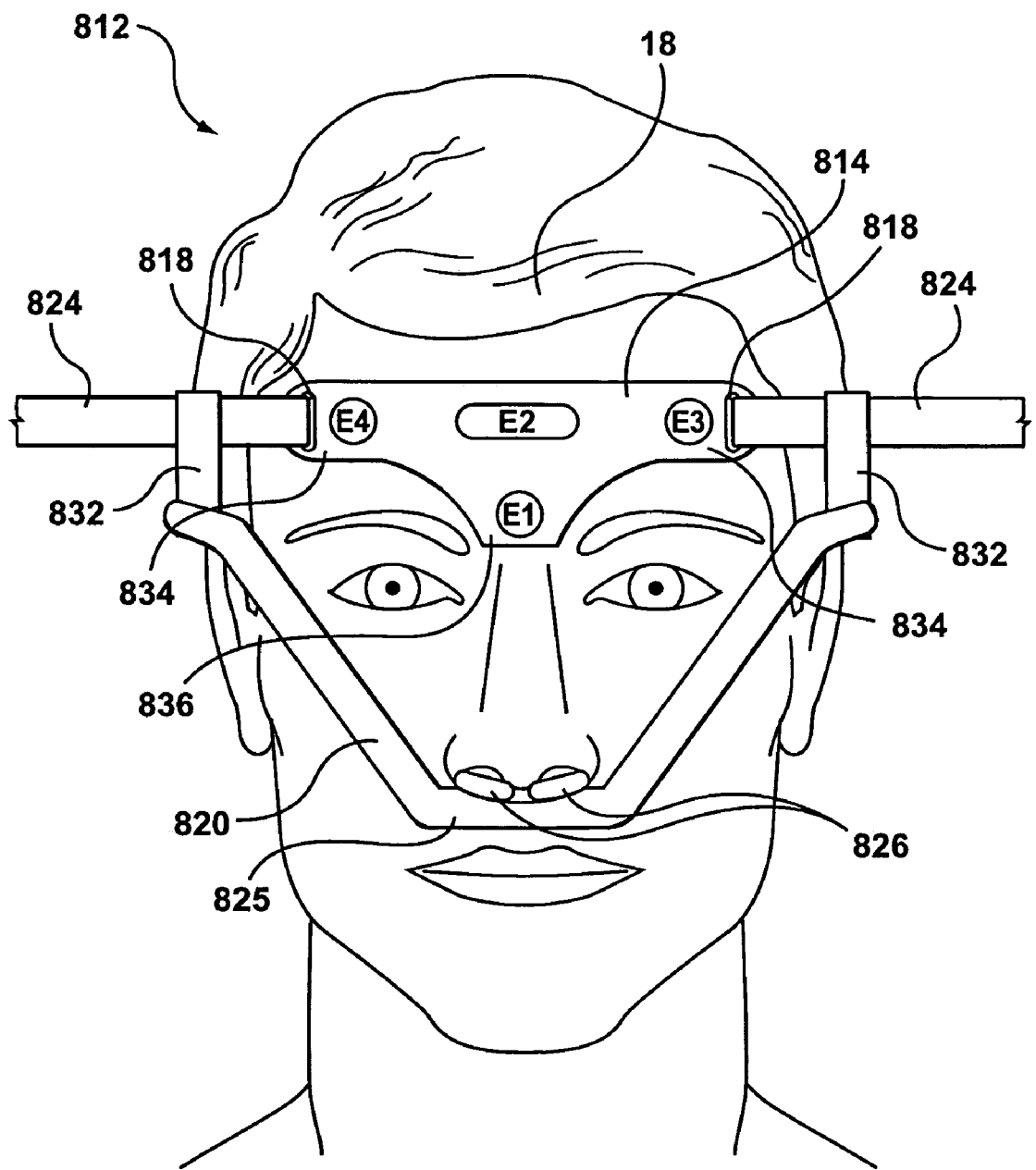
FIG. 8 is a front view of another mask assembly according to yet another embodiment.

Referring now to FIG. 8, there is shown a mask assembly 812 according to another embodiment. Mask assembly 812 is similar to mask assembly 712, except that it uses an alternative nasal interface 820. Mask assembly 812 has a flexible forehead plate 814 and strap 824, which are the same as forehead plate 714 and 712, respectively. As mask assembly 812 is substantially similar to mask assembly 712, the same reference numerals are used to indicate the same features and functions as between the embodiments, except that the reference numerals in FIG. 8 all begin with an "8" in the hundreds column, as compared to the "7" in the hundreds column shown in FIG. 7. Because of these similarities, and in order to avoid repetition, we will only describe the features of the embodiment shown in FIG. 8 that are different to the features of the embodiment shown in FIG. 7.

Nasal interface 820 is of a slightly different form then nasal interface 720, whereby the gas supply tube (not shown) feeds into nasal interface 820 via a tubing loop that extends across the cheeks of the wearer and around to the back of the head or neck, rather than looping upwardly around the nose (as in FIG. 7). Nasal interface 820 is connected to forehead plate 814 via strap 824 using flexible connectors 832. Flexible connectors 832 serve to maintain lip portion 825 and gas outlets 826 in place against the wearer's nose by pulling up the tubing so that it passes above the ears or across the top of the ears of the wearer as it passes around to the back of the wearers head.

Forehead plates 714 and 814 are preferably formed using printed circuit sensors and electrodes, such as those supplied by Vermed, Inc. of Vermont, USA, under the trade name Pc-Sensor. Other forms of flexible printed circuit devices which may be used to form forehead plate 714 to 814 are made by Conductive Technologies, Inc. of York, Pa., USA.

Alternatively, more conventional electrodes may be used within a flexible forehead plate formed of molded plastic, such as a polyvinyl chloride (PVC) plastic. Preferably, the plastic is relatively thin and flexible to accommodate the contours of the wearer's forehead, while having sufficient structural integrity and rigidity to maintain the electrodes in their respective positions and to enable suitable attachment of the straps 724, 824.

The nasal interface 720, which loops around the wearers nose, from across the central forehead, may be of a form similar to that supplied by AEIOMed, Inc. of Minnesota, USA, based on its aura interface. A nasal interface of a kind similar to nasal interface 820 may be obtained from InnoMed Technologies, Inc., of Florida, USA based on their Nasal-Aire™ product line. It should be noted that, while FIGS. 7 and 8 show only one strap for securing the mask assembly to the wearer's head, additional straps may be used in a manner similar to the straps shown and described in relation to FIGS. 1, 2A, 2B, 3, 4 and 5A. Also, if desired, one or more of the electrodes of mask assembly 712, 812 may be located on a part of the strap 724, 824 or on additional straps not shown.

It should be understood that features shown and described in relation to each of the embodiments may be used in combination or substitution with any features of the other described embodiments, where such a combination or substitution would not result in an unworkable arrangement or configuration. Accordingly, the present invention is contemplated to encompass all such combinations or substitutions resulting in operative embodiments.

It should be understood that various modifications can be made to the embodiments described and illustrated herein, without departing from the invention. For instance, the invention is applicable to other types of gas delivery devices such as variable positive air pressure devices, demand positive pressure devices and other variations of such devices. The invention can also be used in other instances where an individual wears a mask as well as sensors for gathering physiological data such as in critical care units. In addition, it should be understood that the particular masks shown herein are shown as examples and that the invention is applicable to other mask designs.

The invention claimed is:

1. A mask assembly adapted to be worn by a wearer for treatment of a medical condition, comprising:
   a mask shaped to fit over at least the nose of the person, the mask including a gas inlet for providing pressurized gas to the wearer;
   a harness assembly attached to the mask, the harness assembly including a plurality of straps for securing the mask assembly to the head of the wearer; and
   sensors located on at least one of the mask and the harness assembly for providing physiological information about the person for determining efficacy of treatment and/or for varying operational parameters of the treatment, wherein the sensors include a first electrode for positioning adjacent a nasion area of the head of the wearer, a second electrode for positioning at a first forehead area of the wearer, and a third electrode for positioning at a second forehead area laterally separated from the first forehead area.

2. The mask assembly of claim 1, wherein the first, second and third electrodes are positioned in a triangular configuration.

3. The mask assembly of claim 1, wherein the mask includes a vertical mounting plate extending upwardly from the top of the mask and wherein the first electrode is located on the mask and a fourth electrode is located on the vertical mounting plate at the central forehead region of the person.

4. The mask assembly of claim 1, wherein the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, wherein the first electrode is located on the mask, the second electrode is located the upper right strap horizontally offset with respect to the center of the right eye of the wearer, and the third electrode is located on the upper left strap horizontally offset with respect to the center of the left eye of the wearer.

5. The mask assembly of claim 1, wherein the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, right and left lower straps that engage elongated apertures at the bottom of the mask, a right vertical strap behind the right ear of the wearer that connects the right upper strap to the right lower strap and a left vertical strap behind the left ear of the wearer that connects the left upper strap to the left lower strap, the right and left vertical straps located proximally to the right and left mastoids of the wearer, wherein the second electrode is located at the upper right strap horizontally offset with respect to the center of the right eye of the wearer, the third electrode is located at the upper left strap horizontally offset with respect to the center of the left eye of the wearer, and a fourth electrode is located at one of the right and left vertical straps proximally to the corresponding mastoid of the wearer.

6. The mask assembly of claim 1, wherein the mask includes a vertical mounting plate extending upwardly from the top of the mask and a forehead support member attached horizontally therewith, the forehead support member having vertically elongated apertures at either end, and wherein the harness assembly includes right and left upper straps that engage the corresponding elongated aperture on the forehead support member, right and left lower straps that engage elongated apertures at either side near the bottom of the mask, a right vertical strap behind the right ear of the wearer that connects the right upper strap to the right lower strap and a left vertical strap behind the left ear of the wearer that connects the let upper strap to the left lower strap, the right and left vertical straps located proximally to the right and left mastoids of the wearer, wherein a fourth electrode is located at the vertical mounting plate at the central forehead region of the wearer and a fifth electrode is located at one of the right and left vertical straps proximally to the corresponding mastoid of the wearer.

7. The mask assembly of claim 1, wherein the mask includes a forehead support member extending vertically from the top of the mask, the forehead support member having right and left horizontal ends that extends above the eyebrows of the wearer, wherein the first electrode is located on the mask, the second electrode is located on the right horizontal end of the forehead support member above the right eyebrow of the wearer and horizontally offset with respect to the center of the right eye of the wearer, and the third electrode is located on the left horizontal end of the forehead support member above the left eyebrow of the wearer and horizontally offset with respect to the center of the left eye of the wearer.

8. The mask assembly of claim 1, wherein the sensors further include a blood oximeter sensor.

9. The mask assembly of claim 8, wherein the mask includes a forehead support member extending vertically therefrom, the blood oximeter sensor being located at the forehead support member in close proximity to the forehead of the wearer.

10. The mask assembly of claim 1, wherein the sensors further include a pressure transducer sensor disposed within the mask.

11. The mask assembly of claim 1, wherein the sensors further include a position sensor.

12. The mask assembly of claim 1, wherein the mask includes a forehead support member extending vertically therefrom, the position sensor being located at the forehead support member.

13. The mask assembly of claim 1, wherein the sensors further include at least two of a blood oximeter sensor, a pressure transducer and a position sensor.

14. The mask assembly of claim 1, wherein the mask assembly further includes a remote processing unit connected to the sensors for processing the physiological information.

15. The mask assembly of claim 14, wherein the remote processing unit includes a sleep efficacy algorithm for processing the physiological information and generating a sleep information profile for the wearer.

16. The mask assembly of claim 14, wherein the remote processing unit includes a wireless transceiver for wirelessly transmitting signals related to the physiological information, and a battery for providing power to the remote processing unit.

17. A mask assembly adapted to be worn by a wearer for treatment of a medical condition, comprising:
a mask shaped to fit over at least the nose of the wearer, the mask including a gas inlet for providing pressurized gas to the wearer;
a harness assembly attached to the mask, the harness assembly including a plurality of straps for securing the mask assembly to the head of the wearer; and
a plurality of electrodes located on the inside of at least one of the mask and the harness assembly and being spaced with regards to one another for sensing physiological information including at least one of the EEG, EMG and EOG of the wearer whereby the physiological information is used to monitor the efficacy of treatment or to vary operational parameters of the treatment, wherein the sensors include a first electrode for positioning adjacent a nasion area of the head of the wearer, a second electrode for positioning at a first forehead area of the wearer, and a third electrode for positioning at a second forehead area laterally separated from the first forehead area.

18. A mask assembly adapted to be worn by a wearer for treatment of a medical condition, the mask assembly including sensors located on the mask assembly for sensing physiological information from the wearer and a remote processing unit located on the mask assembly and connected to the sensors for processing the physiological information, wherein the sensors include a first electrode for positioning adjacent a nasion area of the head of the wearer, a second electrode for positioning at a first forehead area of the wearer, and a third electrode for positioning at a second forehead area laterally separated from the first forehead area.

19. A mask assembly for wearing by a wearer during treatment of a medical condition, the mask assembly comprising:
a nasal interface for providing pressurized gas to the wearer, the nasal interface comprising a gas inlet for receiving a source of gas and a gas outlet for providing gas directly to the nares of the wearer;

at least one strap connected to the nasal interface for securing the mask assembly to the head of the wearer; and a forehead member for location on a forehead of the wearer, the forehead member comprising sensors for measuring physiological signals of the wearer during treatment of the medical condition, wherein the sensors include a first electrode for positioning adjacent a nasion area of the head of the wearer, a second electrode for positioning at a first forehead area of the wearer, and a third electrode for positioning at a second forehead area laterally separated from the first forehead area.

20. The mask assembly of claim 19, wherein the first, second and third electrodes are disposed so as to contact the skin of the forehead of the wearer during the treatment and to sense the physiological signals.

21. The mask assembly of claim 20, wherein the second electrode is disposed on the forehead member so as to overlie a portion of the forehead of the wearer vertically above the nasion.

22. The mask assembly of claim 19, wherein the forehead member, when worn by the wearer, extends laterally across the wearer's forehead and has a lower portion that at least partly overlies the nasion area of the wearer.

23. The mask assembly of claim 22, wherein the first electrode is disposed on the lower portion of the forehead member and the second and third electrodes are disposed on lateral extensions of the forehead member.

24. An electrode placement assembly for locating electrodes on a forehead of a wearer of the electrode placement assembly, comprising:

a forehead placement assembly dimensioned to extend laterally across the forehead of the wearer and having a lower portion for at least partly overlying a nasion area of the wearer;

at least one strap connected to the forehead placement assembly for securing the electrode placement assembly to the wearer; and a plurality of electrodes positioned on at least one of the forehead placement assembly and the at least one strap so that the plurality of electrodes contact the skin of the wearer, wherein the sensors include a first electrode for positioning adjacent a nasion area of the head of the wearer, a second electrode for positioning at a first forehead area of the wearer, and a third electrode for positioning at a second forehead area laterally separated from the first forehead area.

25. The assembly of claim 24, further comprising attachment means for attaching a nasal interface to the electrode placement assembly so that the nasal interface is positioned to provide gas to the nares of the wearer.

26. The assembly of claim 25, wherein the attachment means comprises flexible attachment members for attaching the nasal interface to the at least one strap.

27. The assembly of claim 25, wherein the attachment means comprises a connector member positioned on the forehead placement assembly for connecting the nasal interface to the forehead placement assembly.

28. The assembly of claim 24, wherein the forehead placement assembly comprises a flexible unitary plate.

29. The assembly of claim 24, further comprising a fourth electrode located on the forehead placement assembly to be positioned on the forehead of the wearer between the second and third electrodes.

* * * * *

UNITED STATES PATENT AND TRADEMARK OFFICE
CERTIFICATE OF CORRECTION

| | |
|---|---|
| PATENT NO. | : 7,575,005 B2 |
| APPLICATION NO. | : 11/131284 |
| DATED | : August 18, 2009 |
| INVENTOR(S) | : John Robert Mumford, Ronald Leon Kurtz and Jianping Wu |

It is certified that error appears in the above-identified patent and that said Letters Patent is hereby corrected as shown below:

Claim 4 of the above-referenced patent contains a typo. At Claim 4, at column 19, line 11 the word "on" should be added after the word "located". At Claim 12, at column 20, line 13, the number "1" should be deleted and the number "11" substituted in its place.

Signed and Sealed this
Twenty-eighth Day of December, 2010

David J. Kappos
*Director of the United States Patent and Trademark Office*